United States Patent [19]

Ries et al.

[11] 4,311,905

[45] Jan. 19, 1982

[54] FILM STRIP POSITIONING FOR X-RAY TESTING OF PIPES

[75] Inventors: Karl Ries, Mülheim; Kurt Hannoschöck, Sonsbeck; Krsto-Marijan Rozic, Düsseldorf; Günter Basler, Ahrensburg; Harald Sperl, Grosshansdorf; Kurt Weinschenk, Schenefeld, all of Fed. Rep. of Germany

[73] Assignees: Mannesmann Aktiengesellschaft, Düsseldorf; Rich. Seifert & Co. GmbH & Co. KG, Ahrensburg, both of Fed. Rep. of Germany

[21] Appl. No.: 880,549

[22] Filed: Jul. 31, 1978

[30] Foreign Application Priority Data

Feb. 11, 1977 [DE] Fed. Rep. of Germany ....... 2706346

[51] Int. Cl.³ ............................................. G03B 41/16
[52] U.S. Cl. .............................. 250/321; 250/358 P; 250/444

[58] Field of Search .................... 250/358 P, 491, 320, 250/321, 444

[56] References Cited

U.S. PATENT DOCUMENTS 3,686,932  8/1972  Ries et al. ............ 250/358 P
4,060,727 11/1977  Verdickt ............. 250/358 P Primary Examiner—Davis L. Willis
Attorney, Agent, or Firm—Smyth, Pavitt, Siegemund & Martella

[57] ABSTRACT

An apparatus for X-ray testing of pipes following ultrasonic testing includes a reversible roller track for telescoping a pipe upon a cantilever arm which can be moved up and down on a stand and carrying an endless belt with resilient U-shaped holders for supporting film strips to be moved into the pipe and adjacent to suspected defects. Reversal of the belt drive permits removal of the exposed film strips as the pipe is moved out.

9 Claims, 5 Drawing Figures

4,311,905

FILM STRIP POSITIONING FOR X-RAY TESTING OF PIPES

BACKGROUND OF THE INVENTION

The present invention relates to testing of tubes pipes and other hollows, particularly of pipes having thick walls and a large diameter.

A variety of methods are known for inspecting pipes, tubes, etc. for purposes of detecting any defects. One method that is commonly used employs X-rays and equipment for taking X-ray pictures. The German Pat. No. 1,939,933 discloses that an X-ray sensitive film be placed manually onto the pipe prior to moving the pipe into the test chamber in which the X-ray picture is being taken. After the pipe has left that chamber, the exposed film is manually removed. This procedure is time-consuming and may well interfere with the overall procedure which is carried out in sequence of particular steps. This is particularly true if the X-ray test is carried out on line with an ultrasonic testing procedure involving the same tube or pipe and operating on a highly automated basis. Moreover, the inaccuracies inherent in the manual placement necessitate utlization of large film strips just to increase the safety margin. Modern ultrasonic test equipment is frequently used as a preliminary inspection and locating technique to find flaws and defects in a welding seam. The X-ray test is then used to further identify the defect. It is necessary here to correlate the two techniques so as to restrict the X-raying to those locations in the seam for which the ultrasonic tests had indicated the possible presence of a defect.

DESCRIPTION OF THE INVENTION

It is an object of the present invention to provide a new apparatus for positioning film strips to be used for X-ray testing of tubes, pipes and other hollows.

It is another object of the present invention to improve the operation of X-ray testing of such hollows particularly after they have been tested by means of ultrasonic test equipment.

In accordance with the preferred embodiment of the invention, the tube, pipe, etc., to be tested is positioned by means of a roller track to obtain a particular axial position and, preferably, the tube is rotated on its axis to obtain a particular azimuthal position, e.g. of a welding seam to be tested. A cantilever is disposed for up and down movement, is inserted in the pipe and carries an endless belt, preferably made of individual, resilient holding elements of U-shaped cross-section. Individual film strips are placed on the belt and moved inside of the pipe into particular positions in relation to the pipe, being determined by the relative position of the pipe and the film placement device. After the various film strips have been placed and positioned, the arm is raised so that the resilient holders urge the film strips in contact with the pipe and a source of X-rays takes care of the exposure, through the pipe material. After exposure the arm is lowered, and the belt drive reverses to move films to the film strips to a take up and removal device, while the pipe is rolled out of the station, unless for a variety of reasons a second set of film strips are to be placed and exposed. The film strip positions are predetermined, e.g. on the basis of a prior ultrasonic testing, which identified locations of suspected defects.

The apparatus works rather speedily and exact, and avoids errors that may otherwise be incurred due to incorrect manual placement of film strips. The apparatus can particularly be integrated in test equipment in which ultrasonic tests are stepwise performed on one pipe after the other.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows a cantilever arm 1 provided in a given length for accommodating long pipes, and still being longer than them. Cantilever 1 is mounted on a support, post or stand 2 in a manner which permits lowering and raising the arm, whose other end is, of course, unsupported. Reference numeral 2' refers to a chain drive for the arm for moving it up and down on the stand.

Figure 1:
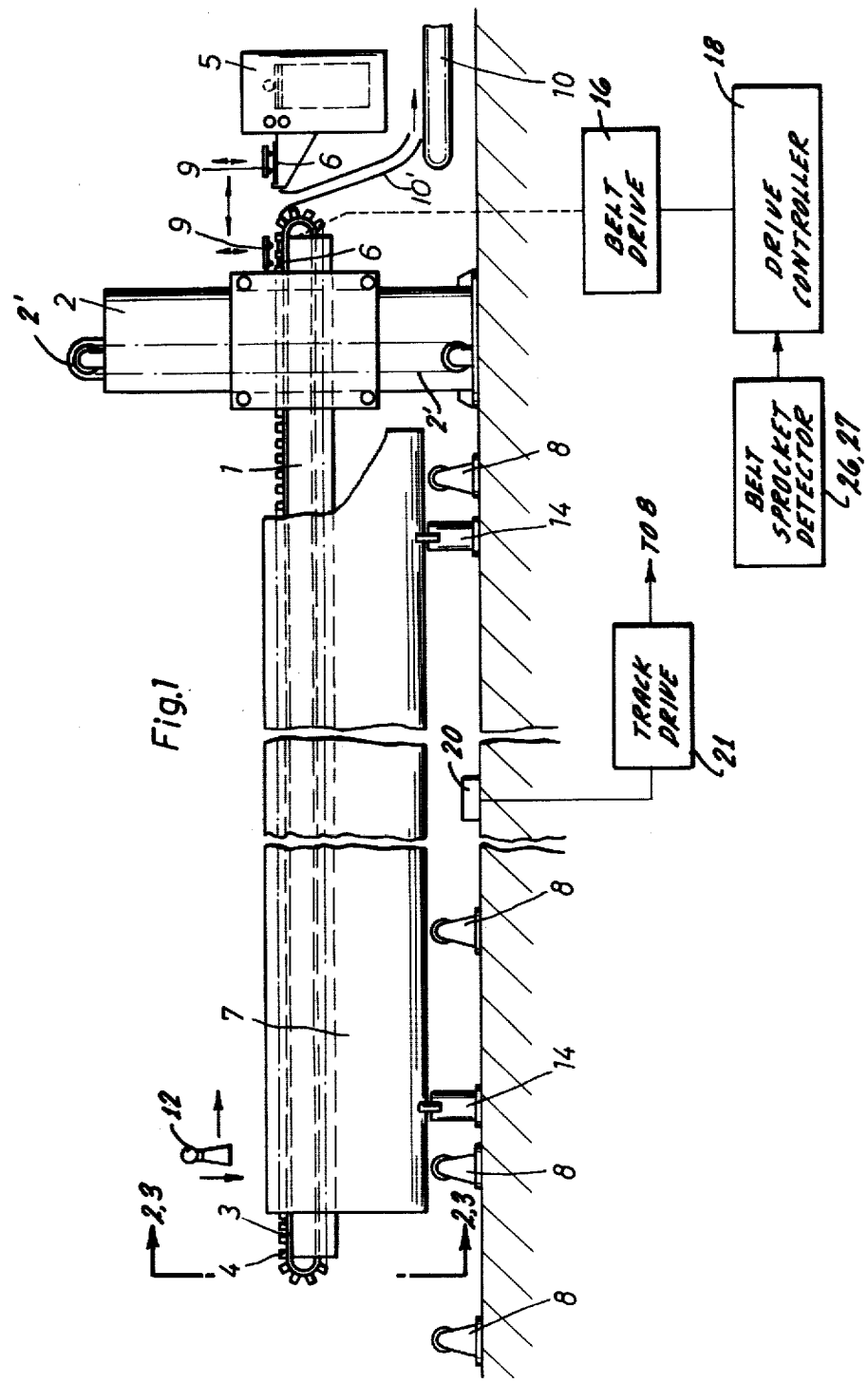
FIG. 1 is a side view of X-ray test equipment for tubes, pipes, etc. and incorporating the features of the invention.

A reversibly driven endless belt 3 is mounted on arm 1 having many U-shaped resilient support elements 4. The arm 1 is hollow and belt 3 runs in one direction through the interior of the arm (from left to right), and above it in the opposite direction. The arm 1 and belt 3 actually extends a little to the rear of support 2 thus having actually a very short arm in opposite direction but, as far as the lever arrangement is concerned, the cantilever aspect dominates.

Reference numeral 5 refers to a feeder device for individual film strips such as 6 placing them in particular sequence within the reach of a film transport device 9. This device 9 picks up an individual strip 6, moves it across (see horizontal double arrow) and lowers the film strip onto the support elements 4 of belt 3 near that one short end of arm 1.

Figure 4:
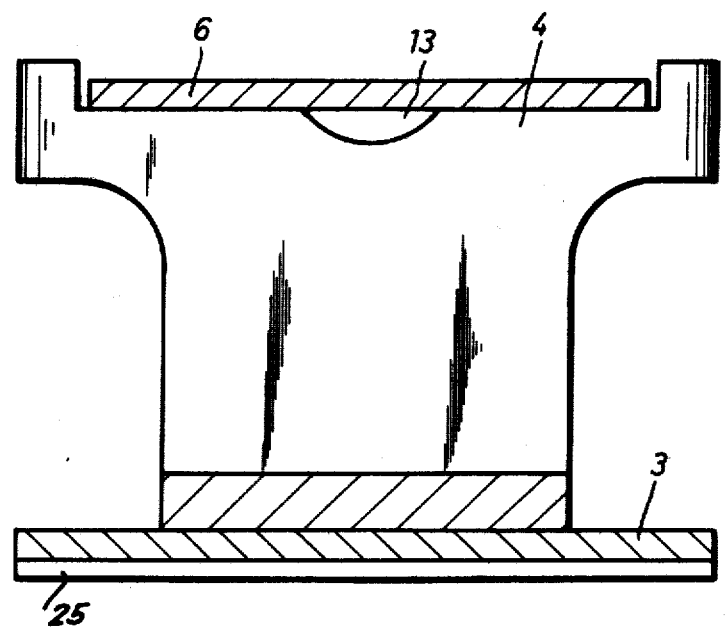
FIG. 4 is a cross-section through a conveyor belt used in FIGS. 1, 2 and 3.
Figure 5:
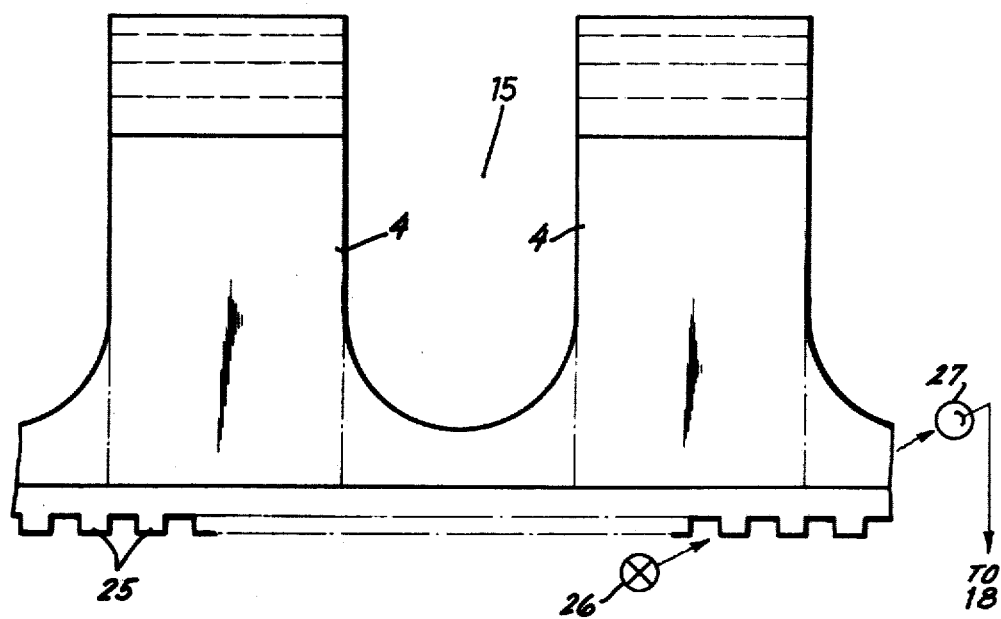
FIG. 5 is a side view of a portion of that belt.

FIG. 4 shows in greater detail that the film 6 is placed on the flat bottom and between the short legs of the U-profile of the resilient supports 4. The U-profile has a central indentation in form of a concave groove 13. The bottom of the U is a little wider than the film strip. Alternatively, the side walls (legs) of the trough defined by the U may taper down. In addition, FIG. 5 shows that the elements 4 are not completely separated but are tooth-like projections with space 15 in-between and projecting from a common backing; all made of resilient, preferably rather soft material. The space or slots 15 can be less wide or may even run all the way through (dash-dot lines). Primary aspect here is that the belt and the support means it provides for the film strips can move around the pulleys which drive the belt without undue tension. Belt 3 is also shown in FIG. 5 to have ribs or teeth to engage sprockets of the drive and pulleys. The teeth 25, however, may have an additional function. A transverse scanner 26/27 (light source and detector) may meter accurately the passage of incremental belt portions, in definite spatial relation to each of the support elements 4, so that upon accurate counting of the passage of the teeth 25, the location and position of the support elements 4 can readily be tracked for purposes of tracking the position and positioning of individual film strips as held on and supported by the support means 4. In view of these teeth, one may use other markings on the belt, even perforations as a means for incrementally identifying the belt and its progress as these markings move past the stationary scanner such as 26/27.

A tube, pipe or other hollow 7 to be tested and inspected is moved longitudinally by means of reversible rollers 8 of a track. This roller track moves the pipe into and out of the test and X-ray chamber. This chamber houses all of the equipment shown in FIG. 1, primarily, however, the equipment shown to the left or stand 2. Reference numeral 14 refers to equipment for turning (rotating) the pipe on its axis for purposes of positioning the welding seam into a particular position, such as a twelve o'clock position. This rotating equipment may cooperate with a suitable scanner for locating the seam. The rotating equipment 14 may additionally be constructed for raising the pipe and lifting it off track rollers 8 and for lowering the pipe back onto the track. Presently, then it is presumed that X-ray inspection be limited to inspecting the seam 17. However, the film placement as per the invention is not limited to that application, though, that is the preferred one. It should be noted that axial movements as well as rotating the pipe permits any portion of the pipe to be placed into particular disposition in relation to any suitably placed film strip on belt 3.

Reference numeral 20 refers to a detector which is suitably placed to monitor a central marking of and on the pipe. The detector 20 is particularly positioned with respect to (a) the arm 1, (b) its extension, and (c) the location of the film placement device 9, particularly where placing film strips onto belt 3. Detector 20 operates and controls the drive 21 for the track 8, to stop the pipe when in a particular position. Thus, the detector 20 causes pipe 7 to stop when its marking has a particular position in relation to the arm 1, which can be termed a zero position.

It can thus be seen that any particular film strip can be placed into a particular position vis-a-vis the pipe and here particularly the welding seam 17 thereof. Once the pipe has been stopped, the film placement device 9 places a film strip 6 onto belt 3 which, in turn, moves the strip into the pipe. The belt drive 16 is controlled to stop adjacent a location of the seam 17 which is accurately predetermined on account of the particular positioning of the pipe. The belt drive 16 is under control of a controller 18 which includes position identification signals for suspected seam flaws. As stated, the pipe may have been previously inspected by means of ultrasonics to find any defect or the like. Having found indications that defects may be present, the ultrasonic test equipment identified the locations of these defects, e.g. by signals representing the distance of the suspected defect for the central marking on the pipe or from one of its ends. The position control for drive 16 may be constructed to stop the drive when the belt has moved by a commensurate distance being, for example, augmented by the distance of the film placement device 9 from the front end of the pipe when the pipe's center marking is aligned with detector 20. Or, if the distance values from the ultrasonic testing have been taken and stored relative to that marking, the controller 18 recalculates a new distance for belt movement by taking the fixed distance between devices 9 and 20 and either adding or subtracting the suspected defect distance depending on whether it is to one side or the other from the central marking. The thus calculated distance is the one needed to move a strip into the requisite position adjacent the suspected fault.

The equipment and apparatus as described operates as follows. The pipe 7 is moved into the equipment chamber by means of roller track 8 and the drive for the track is stopped when the central pipe marking is aligned with detector 20. The seam 17 may have been brought earlier into the twelve o'clock position, particularly because the ultrasonic testing of the seam may have been carried out in the six o'clock position. However, the seam may still require repositioning to be more accurately in the twelve o'clock position, the transfer of the pipe may have caused an angular deflection. Thus, repositioning rollers 14 may now rotate the pipe slightly or to whatever degree is necessary to have the seam 17 in the twelve o'clock position.

Figure 2:
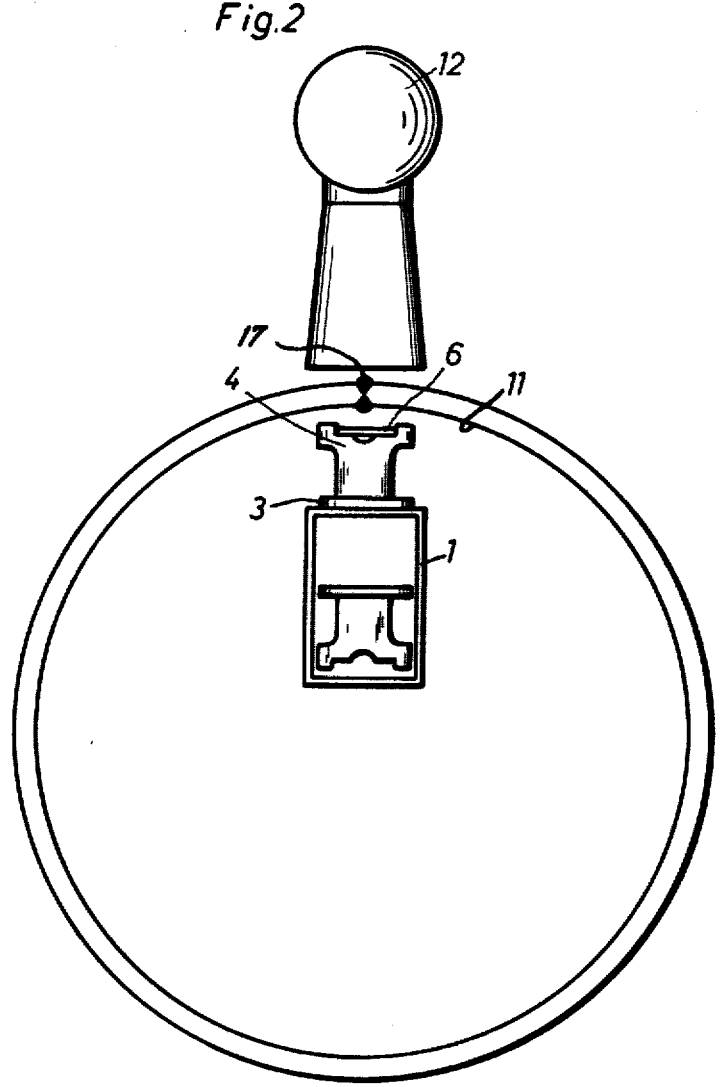
FIGS. 2 and 3 are views along lines 2, 3 of FIG. 1 but on a larger scale and showing different operating positions as between a pipe and particular equipment parts.

The arm 1 has a rather low position when the pipe 7 is being moved in to receive the arm and the belt drive. Also, the X-ray source 12 is up. FIG. 2 illustrates the relative position of the pipe after the pipe has been inserted and, possibly, lifted by the positioning device 14. The pipe may be held by the device 14 throughout the X-raying.

Next, the belt drive 16 is started to move the belt, from a particular starting position, for a distance so that e.g. the portion of the belt adjacent placement device 9 is moved to the end of the pipe adjacent the free end of the arm. This is a precisely predeterminable distance. During belt movement, however, the belt drive is temporarily halted in one or more instances for placement of a film strip 6 by device 9 onto the belt. The detector 26/27 and the calculator in controller 18 track the progression of the belt. The positions of stopping and film placement are chosen so that when the belt drive finally stops, film strips 6 are disposed adjacent all those portions of seam 17 which were "marked" by stored position signals in controller 18 as being suspected as defective. In other words, the drive will stop in those positions for film loading so that the sum total of movement and displacement thereafter and until the final stop, is equal to the distance(s) these flaws have from the placement station. As a consequence, film strips will be found adjacent all the identified suspected flaws.

Figure 3:
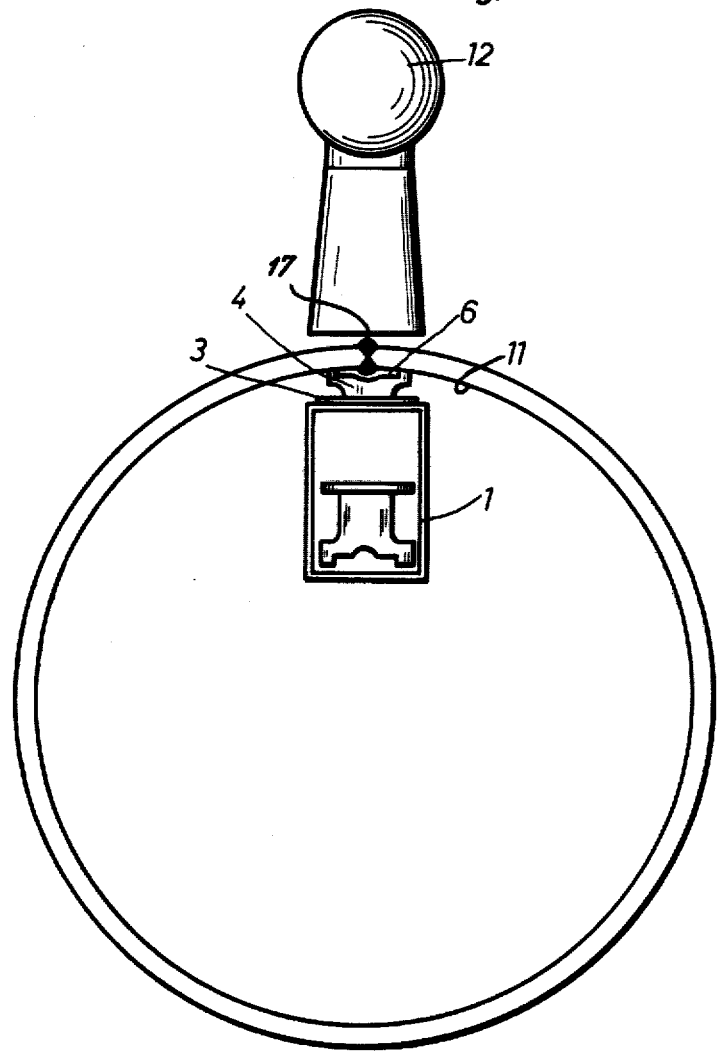

Next, the arm 1 is raised on stand 2 until the holders 4 engage the pipe's inner wall 11 (FIG. 3). In view of the particular configuration of the cross-sectional contour of the holding elements 4 (FIG. 4), the upstanding arms of the U of these resilient elements yield, and the film strip is firmly pressed against the welding seam. The contour 13 in the center of the U permits the film to yield gently to the protruding seam, while the strip is firmly pressed against the tube's wall to both sides of the film. Also, the arm 1 is loaded to a lesser extent by the lateral space between film strip and U as well as by the indent 13. It can be seen further that overall resiliency of the film holder 4 permits the holders to adapt themselves to the curved pipe contour. Any tolerances are also compensated, at least to a considerable extent as the pipe may have slightly varying contour, cross-section etc., over its extension.

Next, the X-ray source 12 is moved along the pipe, stops in the same positions adjacent to which there are film strips and is lowered (see FIG. 3). These positions are well defined by the ultrasonic test results as was outlined above and correspond, of course, to those that caused the placement device 9 to particularly place the film strips on the belt 3.

After all film strips have been exposed, arm 1 is lowered and the belt 3 is reversed. Now all exposed film strips drop one by one, in inverse order of placement and through chute 10' onto a belt 10 to be moved towards the development chamber etc. In the meantime, tube or pipe 7 has been lowered again onto the roller track 8 which reversed also and moves the pipe out of the test station.

Pipe removal as just described, may, however, be deferred in certain cases. For example, the locations or some of the locations to be X-rayed may be so close to each other so that actually one had to place film strips without any gap onto the belt. Since the danger of overexposure of juxtaposed edge portions (upon separate sequential irradication of the juxtaposed film) actually precludes juxtaposing film strips, one may run the test in two steps. In the first run or step one places film strips only on these locations which are at least a certain safety distance apart, leaving out some locations in-between. After exposure and removal of the exposed films from belt 3 onto belt 10, the belt 3 is again loaded with film strips at the remaining locations, and the exposure run is renewed. Only thereafter is pipe 7 placed back onto track 8, and moved out. Of course, one may use as many steps as needed, particularly if one does want to obtain overlapping X-ray pictures.

The entire sequence is automated to such an extent that X-raying the pipe, i.e. certain portions thereof, may not take longer than ultrasonic inspection of the next pipe so that a basically uninterrupted testing sequence can take place with little or no idle times.

The invention is not limited to the embodiments described above but all changes and modifications thereof not constituting departures from the spirit and scope of the invention are intended to be included.

We claim:

1. Apparatus for X-ray testing of pipes, including a source of X-rays, a reversible roller track, and means for rotating the pipe on its axis to provide for a particular azimuthal position of the pipe, further comprising:

- a horizontal cantilever arm mounted for up and down movement on a stand while maintaining a horizontal disposition, and extending above said track parallelly thereto;
- a movable endless belt on the arm with individual film strip holder means on the belt for holding and/or supporting film strips or the like in variable dispositions a pipe when on the roller track and when having been moved towards the stand receiving the arm and the belt in its interior;
- means disposed adjacent to the endless belt, outside said piece, for placing film strips or the like onto the belt;
- controlled drive means for the belt to move the belt so that individual holding means on the belt traverse particular distances from a disposition adjacent to said means for placing to respectively particular predetermined positions adjacent to the pipe; and
- control means for operating the means for placing, to cause individual film strips to be placed onto particular ones of the holding means, for subsequent movement by the drive means and positioning by the belt into the predetermined positions respectively adjacent to predetermined portions of and inside the pipe.

2. Apparatus as in claim 1, said belt being provided with individual resilient holders of U-shaped cross-section.

3. Apparatus as in claim 1, said belt having a resilient layer with transverse cut-outs.

4. Apparatus as in claim 1, including detection means for detecting the position of the pipe relative to the arm.

5. Apparatus as in claim 1, said belt being provided with holding means having U-shaped cross-section.

6. Apparatus as in claim 5, wherein the U is comparatively wide and has a concave indentation in the center.

7. Apparatus as in claim 5, said holding means being resilient for resiliently holding a film strip against the pipe.

8. Apparatus as in claim 1, and including means for particularly positioning the pipe initially relative to the means for placing the film strips.

9. Apparatus as in claim 1, the controlled drive means including means for tracking the belt movement.

* * * * *